US012042475B2

(12) United States Patent
Bocian

(10) Patent No.: US 12,042,475 B2
(45) Date of Patent: *Jul. 23, 2024

(54) NON-SURGICAL LASER TREATMENT FOR A FIBROUS MASS

(71) Applicant: Darin Bocian, Tucson, AZ (US)

(72) Inventor: Darin Bocian, Tucson, AZ (US)

(*) Notice: Subject to any disclaimer, the term of this patent is extended or adjusted under 35 U.S.C. 154(b) by 51 days.

This patent is subject to a terminal disclaimer.

(21) Appl. No.: 17/184,577

(22) Filed: Feb. 24, 2021

(65) Prior Publication Data

US 2021/0244693 A1    Aug. 12, 2021

Related U.S. Application Data

(63) Continuation of application No. 16/365,409, filed on Mar. 26, 2019, now Pat. No. 10,933,041, which is a continuation-in-part of application No. 16/294,799, filed on Mar. 6, 2019, now Pat. No. 10,945,977, which is a continuation of application No. 15/225,402, filed on Aug. 1, 2016, now Pat. No. 10,231,942.

(60) Provisional application No. 62/297,693, filed on Feb. 19, 2016, provisional application No. 62/198,787, filed on Jul. 30, 2015.

(51) Int. Cl.
| A61N 5/06 | (2006.01) |
| A61B 5/055 | (2006.01) |
| A61K 31/192 | (2006.01) |
| A61K 31/277 | (2006.01) |
| A61K 31/522 | (2006.01) |
| A61B 5/00 | (2006.01) |
| A61B 8/08 | (2006.01) |
| A61N 5/067 | (2006.01) |

(52) U.S. Cl.
CPC ............ *A61K 31/192* (2013.01); *A61B 5/055* (2013.01); *A61K 31/277* (2013.01); *A61K 31/522* (2013.01); *A61N 5/0613* (2013.01); *A61B 5/4041* (2013.01); *A61B 8/085* (2013.01); *A61N 5/0622* (2013.01); *A61N 5/067* (2021.08)

(58) Field of Classification Search
CPC .... A61N 5/0613; A61N 5/067; A61N 5/0622; A61B 5/055; A61B 5/4041; A61B 8/085; A61K 31/192; A61K 31/277; A61K 31/522

See application file for complete search history.

(56) References Cited

U.S. PATENT DOCUMENTS 7,883,534 B1 * 2/2011 Crosby ................ A61N 5/0613
                                                        607/90
10,231,942 B2 * 3/2019 Bocian .................. A61B 5/055
(Continued)

OTHER PUBLICATIONS

International Search Report for International Application No. PCT/US2020/025088, dated Aug. 6, 2020; 3 pages.
(Continued)

*Primary Examiner* — Eric D. Bertram
(74) *Attorney, Agent, or Firm* — Greenberg Traurig, LLP

(57) ABSTRACT

Systems and methods for treating a fibrous mass associated with a condition such as Morton's neuroma, plantar fibroma, or Achilles tendinopathy are disclosed. According to illustrative implementations, exemplary methods may comprise identifying a location of the fibrous mass and non-surgically delivering electromagnetic energy to the fibrous mass.

97 Claims, 10 Drawing Sheets

(56) References Cited

U.S. PATENT DOCUMENTS

| | | | |
|---|---|---|---|
| 10,881,627 B1* | 1/2021 | Bocian | A61N 5/0613 |
| 10,933,041 B2* | 3/2021 | Bocian | A61K 31/277 |
| 10,945,977 B1* | 3/2021 | Bocian | A61N 5/0613 |
| 2005/0271340 A1 | 2/2005 | Weisberg et al. | |
| 2006/0129022 A1* | 6/2006 | Venza | A61N 2/008 |
| | | | 600/13 |
| 2007/0213792 A1* | 9/2007 | Yaroslavsky | A61N 5/0613 |
| | | | 607/88 |
| 2007/0219604 A1* | 9/2007 | Yaroslavsky | A61N 5/0613 |
| | | | 607/88 |
| 2007/0219605 A1* | 9/2007 | Yaroslavsky | A61N 5/0613 |
| | | | 607/88 |
| 2011/0105996 A1* | 5/2011 | Mustoe | A61K 9/0019 |
| | | | 424/754 |
| 2013/0066237 A1* | 3/2013 | Smotrich | A61N 5/0619 |
| | | | 604/20 |
| 2013/0310905 A1* | 11/2013 | Crosby | A61N 5/06 |
| | | | 607/90 |
| 2014/0343542 A1* | 11/2014 | Karnik | A61M 5/00 |
| | | | 606/24 |
| 2017/0028217 A1 | 2/2017 | Bocian | |

OTHER PUBLICATIONS

Written Opinion for International Application No. PCT/US2020/025088, dated Aug. 6, 2020; 6 pages.
Lana H. Gimber et al., "Ultrasound Evaluation of Morton Neuroma Before and Aller Laser Therapy", American Journal of Roentgenology, Feb. 2017, 208:2, pp. 380-385.
International Search Report for corresponding International Application No. PCT/US2020/025088, dated Aug. 6, 2020; 3 pages.
Written Opinion for corresponding International Application No. PCT/US2020/025088, dated Aug. 6, 2020; 6 pages.

* cited by examiner

Achilles Tendonosis/Tendinopathy

NON-SURGICAL LASER TREATMENT FOR A FIBROUS MASS

CROSS-REFERENCE TO RELATED APPLICATIONS

This is a continuation of application Ser. No. 16/365,409, filed Mar. 26, 2019, published as US2020/0268696A1, now U.S. Pat. No. 10,933,041, which is a continuation-in-part of application Ser. No. 16/294,799, filed Mar. 6, 2019, now U.S. Pat. No. 10,945,977, which is a continuation of application Ser. No. 15/225,402, filed Aug. 1, 2016, published as US2017/0028217A1, now U.S. Pat. No. 10,231,942, which claims benefit/priority of both U.S. provisional application No. 62/198,787, filed on Jul. 30, 2015, and U.S. provisional application No. 62/297,693, filed on Feb. 19, 2016, all of which are incorporated herein by reference in entirety.

FIELD

This invention relates to a non-surgical treatment for a fibrous mass, such as Morton's neuroma, stump neuroma, plantar fibroma, plantar fibromatosis, plantar fasciitis, plantar fasciopathy, and Achilles tendinopathy.

BACKGROUND

Various fibrous masses associated with the fascia and/or tendons of the human foot have proven to be enigma with regard to attempts to effectively treat or cure such conditions in an efficient or practical manner. As one example, perineural fibrosis with axonal degeneration and vascular proliferation of the common digital nerve of the second or third intermetatarsal space are often referred to as a Morton's neuroma. It is believed that fibrosis along with degeneration of the nerve occurs as a result of mechanical irritation or entrapment between the adjacent metatarsal heads. Pain, tingling and numbness are the most common symptoms. Pain can progress to lifestyle limiting.

Referring now to FIG. 1, Morton's neuroma (also known as Morton neuroma, Morton's metatarsalgia, Morton's neuralgia, plantar neuroma, intermetatarsal neuroma, and interdigital neuroma) is a benign neuroma of an intermetatarsal plantar nerve, most commonly of the second and third intermetatarsal spaces (between 2nd-3rd and 3rd-4th metatarsal heads).

Prior art treatment has included shoe modification, use of orthotic devices, corticosterioid injections, alcohol sclerosing injections, and surgical neurectomy.

A fibroma is a non-cancerous, i.e., benign, fibrous tissue tumor or growth, that can occur anywhere in the body. For example, on the plantar, or the bottom surface of the foot, the fibromas are called plantar fibromas. Unlike plantar warts, which grow on the skin, plantar fibromas grow within the plantar fascia, which is a thickened, fibrous sheet of connective tissue that originates from the plantar aspect of medial tubercle of the calcaneus and extends to the plantar plates of the metatarsophalangeal joints with a function of absorbing shock for the foot during ambulation. The plantar fascia is one of the most important ligamentous bands that maintain the longitudinal arch of the foot.

The etiology of plantar fibromas have not been clearly identified, but it is more than likely multifactorial. The typical etiology is repetitive stress overload to the origin of the plantar fascia, together with other causes, such as weight gain, excessive pronation, occupation-related activity, anatomical variations, altered biomechanics (i.e., gait abnormalities), overexertion, and inadequate foot wear.

Plantar fibromas can develop in one or both feet and the common growth is usually a solitary nodule, though multiple nodules are possible in the same foot. The mid-arch region of the foot is the most common location for planter fibromas to develop. However, plantar fibromas can appear anywhere along the underside of the foot. They can occur in people of any age and gender and will not resolve on their own or become smaller without proper treatment.

Prior art treatment can be divided into conservative and surgical measures. Conservative and prior art non-surgical measures can alleviate the pain of a plantar fibroma, but they will not reduce the mass or prevent the progression of the plantar fibroma. These measures typically include steroid injections, orthotic devices (i.e., orthopedic shoe insoles), anti-inflammatory drugs, and physical therapy. Operative measures are needed when the above measures fail to improve symptoms of the plantar fibroma. However, surgical removal of the plantar fibroma requires outpatient care and may result in a flattening of the arch or development of hammertoes. Recurrence of the plantar fibroma occurs even after surgical measures.

Overview of Some Innovations Herein

Implementations of the disclosed technology pertain to systems and methods for treating a fibrous mass, such as associated with Morton's neuroma, stump neuroma, plantar fibroma, plantar fibromatosis, plantar fasciitis, plantar fasciopathy, and Achilles tendinopathy. In one exemplary aspect, a method may include identifying a location of the fibrous mass, determining a first size of the fibrous mass, non-surgically delivering electromagnetic energy to the fibrous mass, and determining a second size of the fibrous mass. Such method(s) may further include determining the type and quantity of a plurality of treatments to deliver, such as an optimum (e.g., minimum) number of treatments. In some embodiments, when treating the fibrous mass, the method further comprising manipulating the fibrous mass into a position adjacent a surface of the patient's foot.

In certain embodiments, medical imaging techniques, such as ultrasound imaging and magnetic resonance imaging, are used to identify the location of the fibrous mass and to determine the first size of the fibrous mass. In other embodiments, identifying the location of the fibrous mass may further include placing a patient in a supine position, palpating the patient's skin over a suspected location of the fibrous mass, and detecting an audible click when palpating skin directly over the fibrous mass. Other imaging technologies, such as Shear Wave Elastography Imaging (SWEI), may also be utilized to demonstrate efficacy of the innovations herein and/or conclusively establish results or outcomes of the present inventions, such as demonstrating the softening of tissue, increase in elasticity, and other like improvement(s). Further, implementations herein may utilize diagnostic ultrasound with SWEI prior to and following laser treatment. As establish by third-party SWEI testing, reduction(s) in size, change of shape, and decrease in the clarity of margin borders of fibrous masses are seen on ultrasound post laser treatment. Such SWEI evidence also confirms softening of the fibrous mass following completion of treatment. Indeed, clear softening/change of elasticity of the fibrous mass of the fibrous mass, as set forth herein, is identified on these SWEI tests post laser treatment.

In certain embodiments, the delivering electromagnetic energy to the fibrous mass step further comprises emitting electromagnetic energy from a lasing device according to certain parameters that are adjusted based on criteria. Such parameters may include setting a beam diameter of a specified size for the evaluation treatment regimen, adjusting a power of to the lasing device, e.g., such that the electromagnetic energy penetrates tissues to a depth of about 6 mm to about 8 mm, directing the beam onto the location for a specified length of time, and delivering a quantity of pulses of the beam to the location. In some embodiments, a Nd:YAG lasing device may be utilized.

In certain embodiments, a topical medication is applied directly on the skin of the location of the fibrous mass. The topical medication may be selected from a group consisting of cream, gel, ointment, and lotion. In some embodiments, the applying the topical medication step further comprises using a combination of topical medications comprising verapamil, pentoxifylline, and tranilast. In one specific embodiment, the applying the topical medication step further comprises using about 15% verapamil by weight, about 3% pentoxifylline by weight, and about 1% tranilast by weight. In other specific embodiment, the applying the topical medication step further comprises using about 15% verapamil by volume, about 3% pentoxifylline by volume, and about 1% tranilast by volume. Other embodiments are set forth below.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF ILLUSTRATIVE IMPLEMENTATIONS

Aspects of the present innovations are described in the following illustrative implementations of the disclosed technology with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "embodiment," "implementation," "in one embodiment/implementation," "in an embodiment/implementation," and similar language throughout this specification may, but do not necessarily, all refer to the same embodiment or implementation.

The described features, structures, or characteristics of the present innovations may be combined in any suitable manner in one or more embodiments. In the following description, numerous specific details are recited to provide a thorough understanding of embodiments of the invention. It should be recognized, however, that the inventions may be practiced without one or more of the specific details, or with other methods, components, materials, and so forth. In other instances, well-known structures, materials, or operations are not shown or described in detail to avoid obscuring aspects of the invention.

Figure 1:
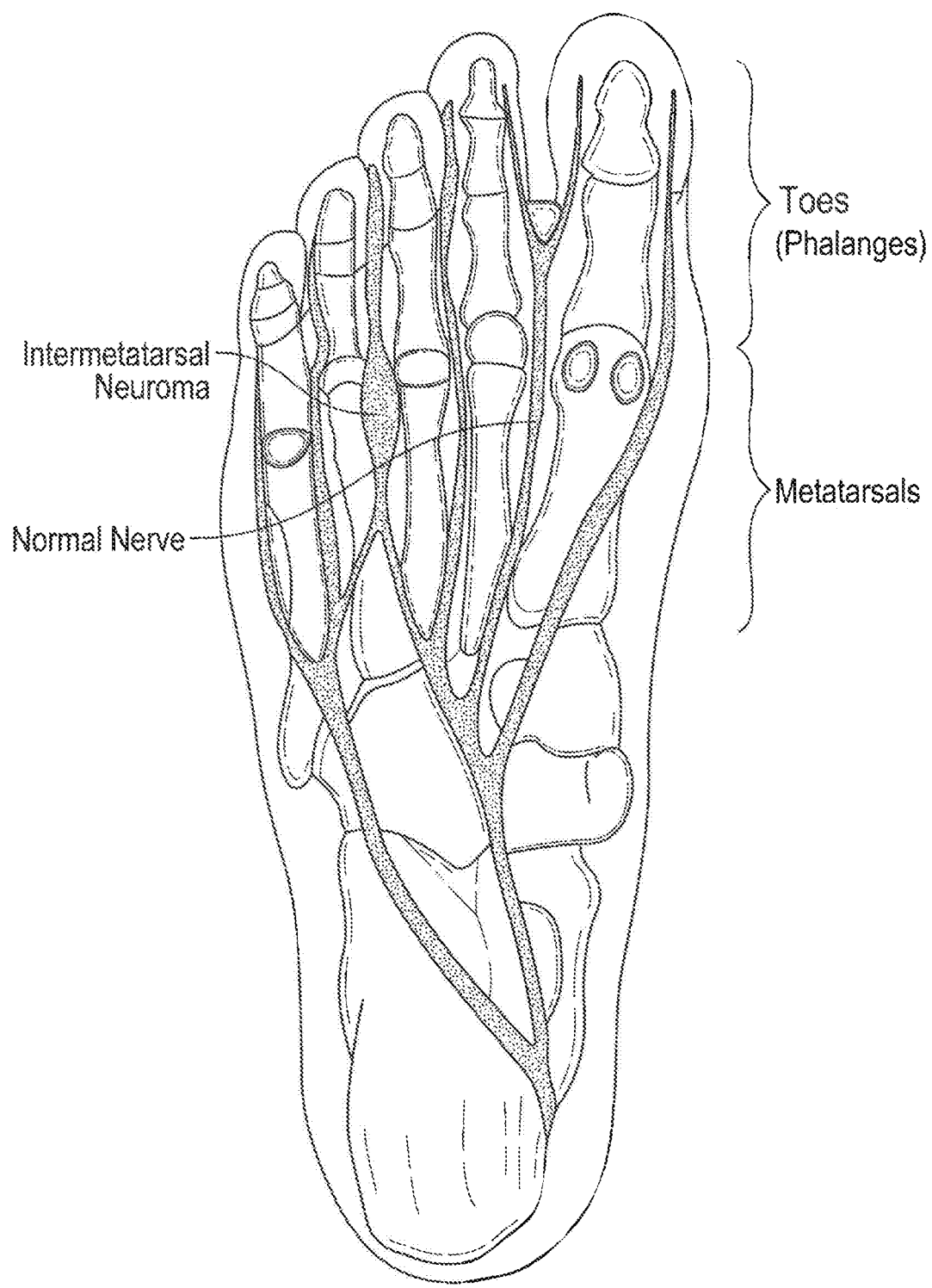
FIG. 1 illustrates the anatomy of the medial plantar nerve and the lateral plantar nerve.

Referring now to FIG. 1, perineural fibrosis of the common digital nerve of the second or third intermetatarsal space is often referred to as a Morton's neuroma. It is believed that fibrosis along with degeneration of the nerve occurs as a result of mechanical irritation or entrapment between the adjacent metatarsal heads. Pain, tingling and numbness are the most common symptoms.

Applicant has found that Morton's neuroma can be effectively treated using non-surgical treatments of laser energy. Surgery is a technology consisting of a physical intervention on tissues, and muscle. As a general rule, a procedure is considered surgical when it involves cutting of a patient's tissues or closure of a previously sustained wound. Applicant's method to treat Morton's neuroma neither involves cutting of a patient's tissues, nor closure of a previously sustained wound.

Other procedures, such as angioplasty or endoscopy, may be considered surgery if they involve "common" surgical procedure or settings, such as use of a sterile environment, anesthesia, antiseptic conditions, typical surgical instruments, and suturing or stapling. Applicant's method to treat Morton's neuroma does not require a sterile environment, anesthesia, antiseptic conditions, surgical instruments, suturing, or stapling.

Figure 2:
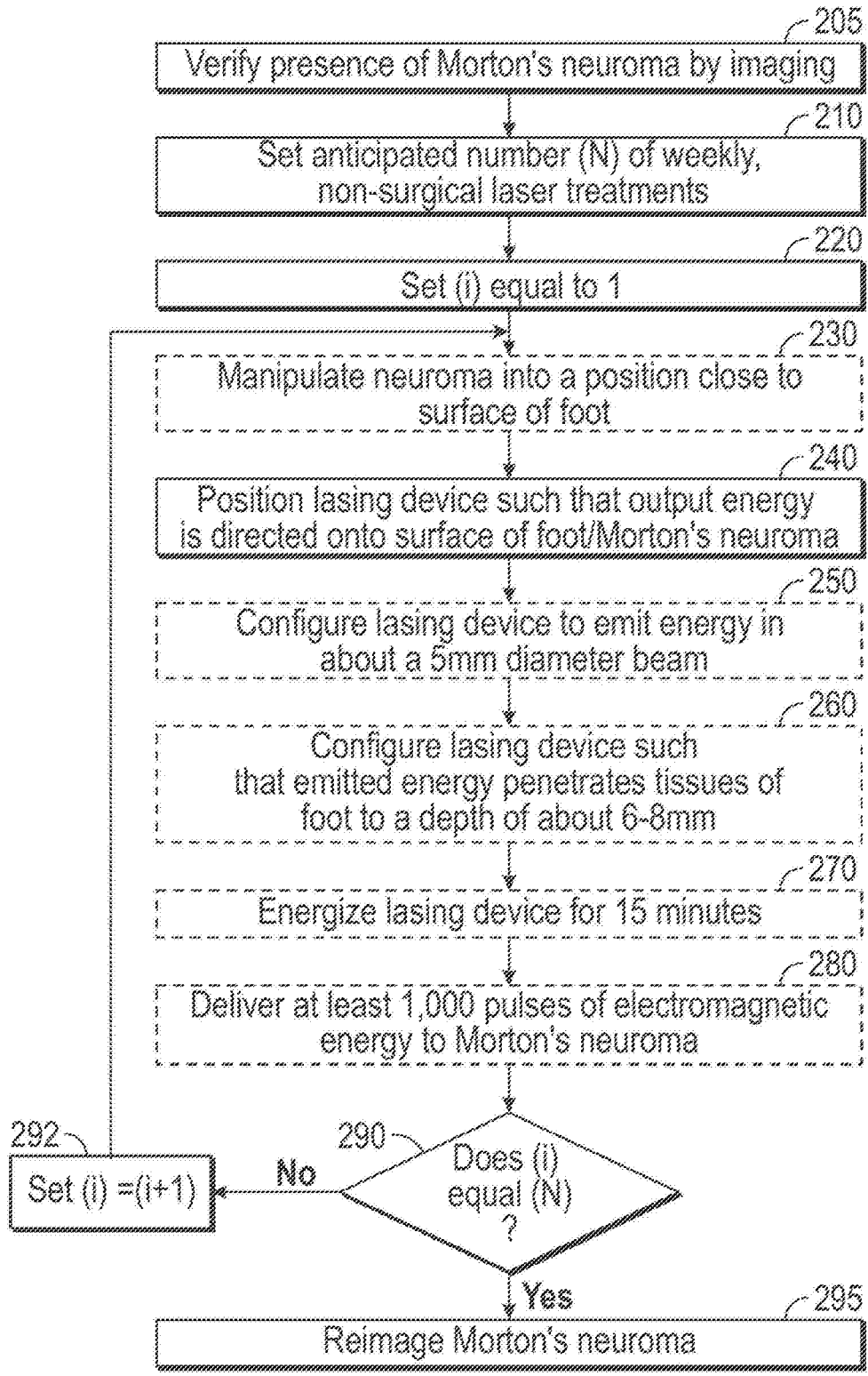
FIG. 2 is a flowchart summarizing the steps of Applicant's method for treating Morton's neuroma.

FIG. 2 summarizes the steps of Applicant's method for treating Morton's neuroma.

Referring now to FIG. 2, in step 205 the method verifies the presence of a Morton's neuroma using one or more medical imaging techniques. Such medical imaging techniques include, without limitation magnetic resonance imaging ("MRI") and/or ultrasound imaging.

In certain embodiments, the target area of the neuroma is identified using Applicant's "Dull Probe Technique," wherein that technique includes using a dull probe while patient is in the supine position, palpating the intermetatarsal space to elicit pain consistent with their chief complaint and/or a positive Mulder's sign (an audible click). A diagnostic ultrasound is also used to identify the specific location of the neuroma. The target area is marked on the plantar surface of foot to guide laser treatment.

In step 210, and based upon the medical imaging of step 210, set an anticipated number of weekly, non-surgical laser treatments. In step 220, the method sets a variable (i) to 1.

In step 230, the method manipulates the verified Morton's neuroma into a position adjacent to a surface of the patient's foot. In step 240, the method positions a lasing device such that output power emitted by that lasing device is directed onto the surface of the patient's foot directly over the plantar surface of the Morton's neuroma.

In certain embodiments, step 230 further comprises applying a topical medication to the surface of the foot directly over top of the Morton's neuroma. According to embodiments herein, the applying the topical medication step may further comprise using a combination of topical medications including verapamil, pentoxifylline, and tranilast. In some specific embodiments, the topical medication may be made by a compounding pharmacy and may comprise Verapamil 15%, Pentoxifylline 3% and Tranilast 1%. The medication is applied just prior to the laser treatment and is allowed to absorb.

Applicant's topical medication is used to treat fibrotic conditions, like plantar fibromas and Dupuytren contracture and scarring. Applicant has found that use of this topical medication assists treatment of the fibrosis around the nerve when used with the Nd:YAG laser.

In certain embodiments, the lasing device of step 240 comprises a Nd:YAG laser.

In step 250, the method configures the lasing device of step 240 to emit electromagnetic energy in a beam of a about 5 mm spot size diameter. In step 260, the method configures the lasing device such that electromagnetic energy emitted by that lasing device penetrates tissues of the foot to a depth of between 6 mm and 8 mm. Applicant has demonstrated with magnetic resonance imaging that this tissue depth is sufficient to reach the candidate nerve.

In step 270, the method energizes the lasing device for about 10 to about 15 minutes. In step 280 in certain embodiments, the method non-surgically delivers about 1,000 pulses of electromagnetic energy at 15 J/cm·sup·2, 6 msec and 7 Hz to the Morton's neuroma. Step 180 does not include cutting of the patient's skin. More specifically, step 180 does not include cutting the patient's skin disposed over or adjacent to the palpated Morton's neuroma. Step 180 does not include closure of a previously sustained wound.

In step 280 in certain embodiments, the method non-surgically delivers about 1,000 pulses of electromagnetic energy to the Morton's neuroma.

In step 290, the method determines if (i) equals (N). If the method determines in step 290, that (i) does not equal (N), then the method transitions from step 290 to step 292 wherein the method increments (i) by 1, i.e. sets (i) equal to (i+1), The method then transitions from step 292 to step 230 and continues as described herein.

If the method determines in step 290, that (i) does equal (N), then the method transitions from step 290 to step 295 wherein the method reimages the Morton's neuroma.

Figure 3:
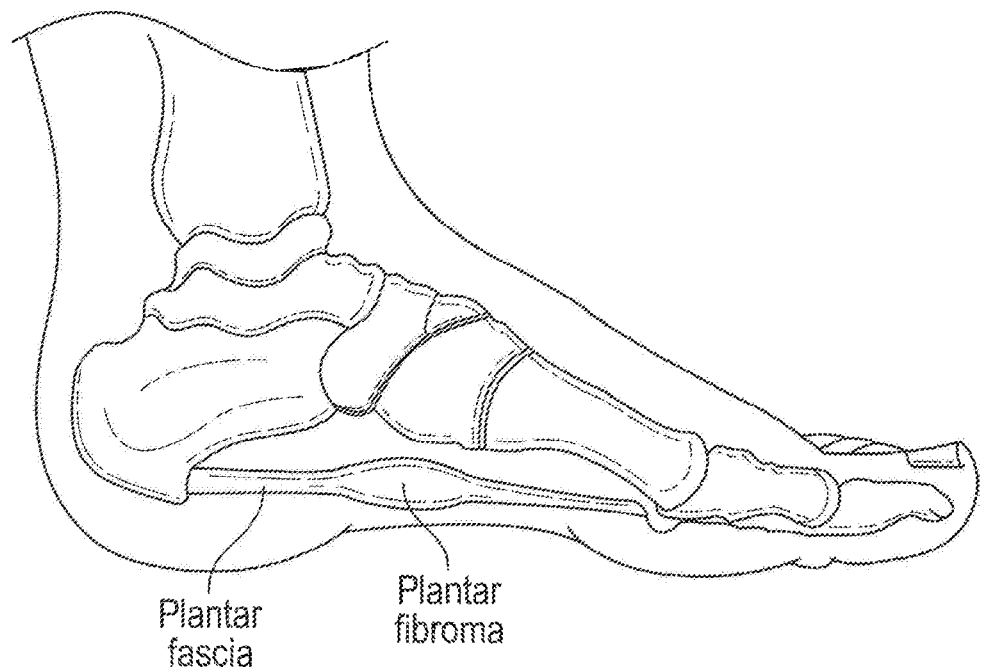
FIG. 3 illustrates the anatomy of the plantar fascia and the plantar fibroma.

Referring now to FIG. 3, a fibrous knot or nodule that is embedded within the planter fascia is often referred to as a plantar fibroma. More invasive, rapid-growing fibromas are considered plantar fibromatosis. The characteristic sign of a plantar fibroma is a noticeable lump in the arch or instep, between the heel pad and the forefoot pad. The typical plantar fibroma appears as a focal, often oval-shaped area with disorganization within the plantar fascia. Larger lesions may be lobulated and can demonstrate a central scar-like appearance with fibers radiating from the plantar fascia. The mass will cause a soft convexity in the contour of the bottom of the foot that may be painful with pressure. Also, prolonged walking and wearing shoes can cause pain or discomfort. In some cases, the mass of the plantar fibroma can progress to cause pain to limit patients' lifestyles.

Applicant has found that plantar fibromas can be effectively treated using non-surgical treatments of laser energy. Surgery is a technology consisting of a physical intervention on tissues, and muscle. As a general rule, a procedure is considered surgical when it involves cutting of a patient's tissues or closure of a previously sustained wound. Applicant's method to treat plantar fibromas neither involves cutting of a patient's tissues, nor closure of a previously sustained wound.

Other procedures, such as angioplasty or endoscopy, may be considered surgery if they involve "common" surgical procedure or settings, such as use of a sterile environment, anesthesia, antiseptic conditions, typical surgical instruments, and suturing or stapling. Applicant's method to treat plantar fibromas does not require a sterile environment, anesthesia, antiseptic conditions, surgical instruments, suturing, or stapling.

Figure 4:
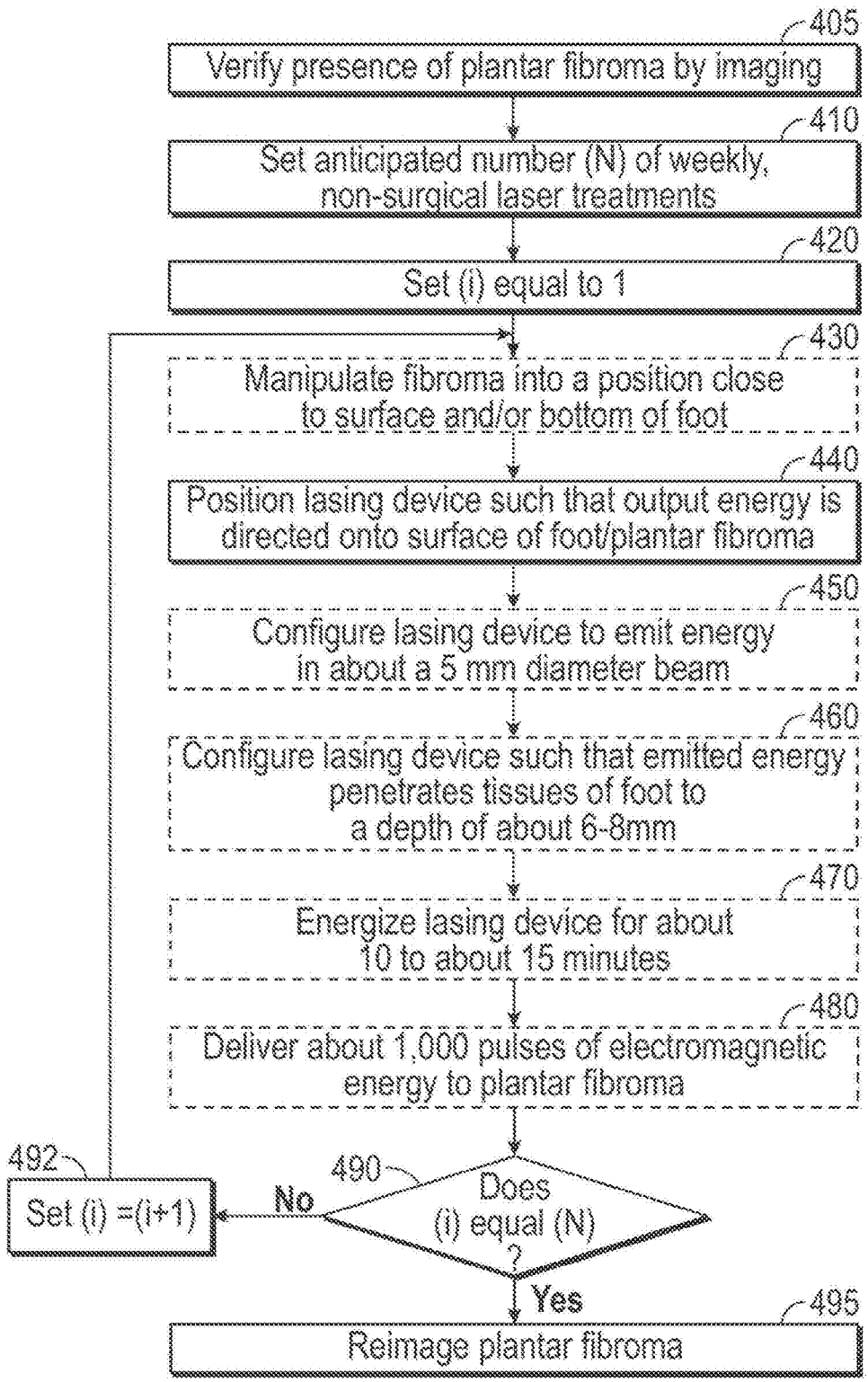
FIG. 4 is a flowchart summarizing the steps of Applicant's method for treating plantar fibroma.
Figure 5A:
FIG. 5A is an ultrasound image showing a plantar fibroma before the laser treatment.
Figure 5B:
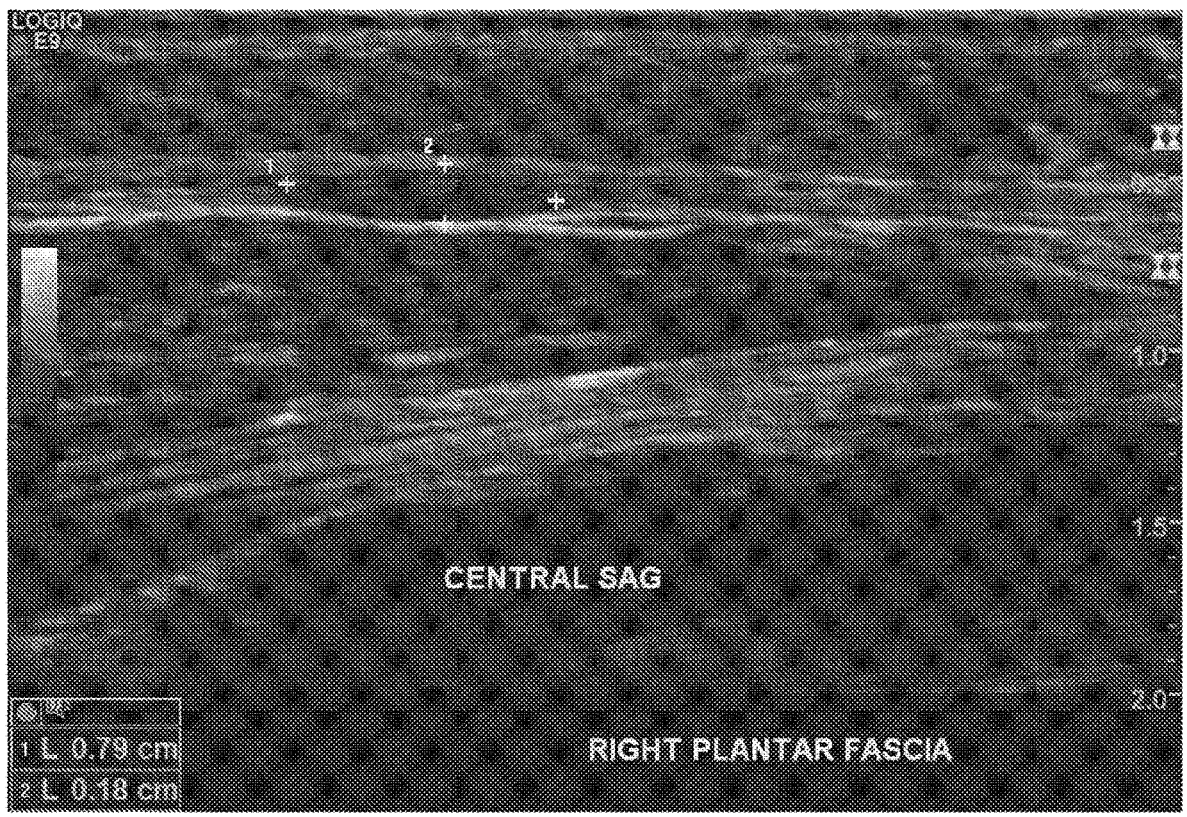
FIG. 5B is an ultrasound image showing a plantar fibroma that is reduced in size after the laser treatment, according to aspects of the innovations herein.

FIG. 4 summarizes the steps of Applicant's method for treating plantar fibroma. Referring now to FIG. 4, in step 405 the method verifies the presence of a plantar fibroma using one or more medical imaging techniques. Such medical imaging techniques include, without limitation, magnetic resonance imaging ("MM") and/or ultrasound imaging.

In certain embodiments, the target area of the fibroma is identified using Applicant's "Dull Probe Technique," wherein that technique includes using a dull probe while patient is in the supine position, palpating the arches of the foot to elicit pain consistent with his/her chief complaint. A diagnostic ultrasound is also used to identify the specific location of the fibroma. The target area (including size, shape, and boarders of the plantar fibroma) is marked on the plantar surfaces and/or the arches of foot to guide laser treatment.

In step 410, and based upon the medical imaging of step 410, the method sets an anticipated number of weekly, non-surgical laser treatments. In step 420, the method sets a variable (i) to 1. In certain embodiments, the anticipated number of weekly, non-surgical laser treatments equals to 10.

In step 430, the method manipulates the verified plantar fibroma into a position adjacent to a surface and/or a bottom of the patient's foot. In step 440, the method positions a lasing device such that output power emitted by that lasing device is directed onto the surface of the patient's foot directly over the plantar fibroma.

In certain embodiments, step 430 further comprises applying a topical medication to the area of the foot directly over top of the plantar fibroma. In some implementations, the topical medication, which can be made in the form of cream, gel, ointment, and lotion, may be made by a compounding pharmacy. According to embodiments herein, the applying the topical medication step may further comprise using a combination of topical medications including verapamil, pentoxifylline, and tranilast. In some specific example, a topical medication in the form of cream may comprise Verapamil 15% by weight, Pentoxifylline 3% by weight, and Tranilast 1% by weight. In other example embodiments, the topical medication in the form of a lotion or other medium may comprise Verapamil 15% by volume, Pentoxifylline 3% by volume, and Tranilast 1% by volume. The medication is applied just prior to the laser treatment and is allowed to absorb.

Applicant's topical medication is used to treat fibrotic conditions, like plantar fibromas, Dupuytren contracture, and scar tissues. Applicant has found that use of this topical medication assists treatment of the fibrosis around the plantar fascia when used with the Nd:YAG laser.

In certain embodiments, the lasing device of step 440 comprises a Nd:YAG laser.

In step 450, the method configures the lasing device of step 440 to emit electromagnetic energy in a beam comprising a about 5 mm spot size diameter. In step 460, the method configures the lasing device such that electromagnetic energy emitted by that lasing device penetrates tissues of the foot to a depth of between 6 mm and 8 mm. Applicant has demonstrated with magnetic resonance imaging that this tissue depth is sufficient to reach the candidate plantar fibromas. A sonography study has shown that most plantar fibromas (nodules) are located superficially in the plantar fascia.

In step 470, the method energizes the lasing device for about 10 to about 15 minutes. In step 480, in certain embodiments, the method non-surgically delivers about 2,000 pulses of electromagnetic energy at 15 J/cm·sup·2, 6 msec and 7 Hz to the plantar fibroma. Step 480 does not include cutting of the patient's skin. More specifically, step 480 does not include cutting the patient's skin disposed over or adjacent to the plantar fibroma. Step 480 does not include closure of a previously sustained wound.

In step 490, the method determines if (i) equals (N). If the method determines in step 490, that (i) does not equal (N), then the method transitions from step 490 to step 492 wherein the method increments (i) by 1, i.e. sets (i) equal to (i+1), The method then transitions from step 492 to step 430 and continues as described herein.

If the method determines in step 490, that (i) does equal (N), then the method transitions from step 490 to step 495 wherein the method reimages the plantar fibroma.

The following examples are presented to further illustrate to persons skilled in the art how to make and use the invention. These examples are not intended as a limitation, however, upon the scope of the invention.

EXAMPLE 1

This Example 1 comprises an unsolicited testimonial from a patient of Applicant.

"My Morton's Neuroma symptoms started a few years ago, beginning with bent toes and a tingling, burning sensation on the bottom of my right foot. Dr. Bocian treated me initially with cortisone injections, which worked well for about a year each. Then the symptoms intensified and I felt like I was walking on a marble. Over a few months' time, I was limping badly, causing pain in the left knee and leg. I started actually calculating how many steps I could avoid in daily activities."

In October, I saw Dr. Bocian and asked what we could do short of surgery so I could recover quality of life and normalcy of movement. He told me about his laser treatment and I began the course of 10 immediately. After treatment no. 2, I felt 95% better.

I feel privileged to have been in Dr. Bocian's care and offered his new application of laser technology for Morton's neuroma."

EXAMPLE 2

History: 58-year-old female with bilateral feet Morton's neuroma status post laser therapy for follow-up.

Comparison: Ultrasound of the right and left feet from 02107/2014. Technique: Focused grayscale and power Doppler ultrasound examination of both feet with attention to the forefoot was performed for follow-up bilateral Morton's neuromas.

Right foot: Redemonstrated is a round hypoechoic lesion at the plantar aspect of the second intermetatarsal space between the second and 3rd metatarsal heads which has decreased in size and now measures 0.2·times·0.2·times·0.2 cm (AP×TR×CC), consistent with a Morton's neuroma. Redemonstrated is a small fluid-filled lesion at the plantar lateral aspect of the 3rd metatarsophalangeal joint, measuring 5 mm in length, which is not contiguous with the Morton's neuroma, and may represent a small adventitial bursa or a ganglion cyst. There is no additional soft tissue abnormality at the remaining intermetatarsal spaces.

Left foot: Redemonstrated is a round heterogeneously hypoechoic lesion at the plantar aspect of the second intermetatarsal space between the second and 3rd metatarsal heads which has decreased in size and now measures 0.3·times·0.2·times·0.1 cm (AP×TR×CC), consistent with a Morton's neuroma. Redemonstrated is an additional ill-defined hypoechoic region at the 3rd intermetatarsal space between the 3rd and 4th metatarsal heads which also has decreased in size and n w measures 0.1·times·0.1·times·0′0.1 cm, which may represent an additional small Morton's neuroma. There are no additional soft tissue abnormalities at the remaining intermetatarsal spaces.

Impression: Bilateral second intermetatarsal space Morton's neuromas and left 3rd intermetatarsal space Morton's neuroma which have decreased in size when compared to reference examination.

EXAMPLE 3

Thirty (30) patients underwent a study evaluating the effect of a Nd:YAG laser in the non-surgical treatment of Morton's neuroma. Baseline diagnostic MRI and/or ultrasound exams were used to confirm the presence of a neuroma. A series of weekly laser treatments were given using Applicant's method. Following completion of the treatments, subjects returned for a follow-up MRI and/or ultrasound study.

The results yielded an extremely high patient satisfaction rate. Follow-up comparison studies revealed a decrease in the size of the neuroma.

Of 42 patients undergoing Morton's neuroma evaluation by US, 21 underwent treatment of a total of 32 Morton" neuromas. Retrospective US review of the pre-treatment lesion showed heterogeneously, hypoechoic masses with well-defined borders with associated pain on transducer pressure in 97% (31/32). An associated bursa (3/28) was identified in a minority of cases. Following treatment the lesions remained heterogeneously hypoechoic but most demonstrated ill-defined borders (23/31) with significantly decreased or absent pain with transducer pressure (29/31). Statistical analysis revealed significant differences in appearance of pre and post-treatment lesion borders ($p<0.0001$) and pain with transducer pressure ($p<0.0001$), as well as the presence of an associated intermetarsal bursa ($p<0.05$), which resolved following treatment, but not size. Finally, all neuromas were determined to be better visualized on US compared to MRI.

Example 3 demonstrates that the use of a Nd:YAG laser in the treatment of Morton's neuroma comprises an excellent option with satisfaction rates being superior to previous treatments. This procedure eliminates surgical intervention along with its associated risks and complications. In addition, out of pocket expense for the patient is reduced. Moreover, there is no down time, and therefore, patients may continue to work and enjoy leisure activities such as golfing, cycling and tennis as tolerable throughout the series of treatments.

EXAMPLE 4

History: 57-year-old male with left second inter space Morton's neuroma status post laser therapy. Comparison: Prior left toot ultrasound dated Nov. 10, 2014. Technique: Grayscale and Doppler ultrasound roots views of the left forefoot were obtained.

Findings: There is redemonstration of hypoechoic lesion within the second intermetatarsal space, measuring 0.4·times·0.4·times·0.3 cm (AP·times·TR·times·CC), which is slightly decreased in size compared to prior study measuring 0.4·times·0.5·times·0.3 cm. There is no significant interval change in the echogenicity or echo texture of this lesion. There is no pain with transducer pressure, which is improved compared to prior study. There is no additional lesion within the remaining interspaces of tile left toot.

Impression: There is redemonstration of hypoechoic lesion within the second demonstrates slight interval decrease in size with no pain on transducer pressure, consistent with successful treatment.

EXAMPLE 5

This Example 5 comprises an unsolicited testimonial from a patient of Applicant.

"I became a patient of Dr. Bocian and in April 2015 after being referred by my primary care provider. I had been living with pain from a large plantar fibroma on my right foot for 2 years. The pain had been increasing over the prior 6 months, which caused me to change my lifestyle to avoid jogging, standing for extended time and long hikes. Since February 2015, I would awake with painful cramping of the right foot in greater toe and would need to spend several minutes stretching before I could walk comfortably.

I have had plantar fibroma surgically removed from my left foot twice in years prior to this occurrence in my right foot. Both times my only options were to live with it or surgically remove it. I didn't care for the long, painful and troublesome recovery from the surgery so I avoided going back to the doctor for this new fibroma. After Dr. Bocian explained the option of laser treatment versus surgery, I was still hesitant about the treatment but I did not want to repeat the surgery route of treatment again. So I decided to give laser treatment a try.

The first 3 laser treatments were uncomfortable at times but Natasha (laser technologist) was very quick and skillful at easing the pain. With each further treatment, I noticed that the morning cramping and pain was disappearing and the nodules were getting softer and smaller. By the end of the treatment plan, I was not having any pain or discomfort in my right foot. The only time I had discomfort was after walking barefoot and stepped on a rock right on the fibroma. It did hurt for a few moments.

Since finishing the treatment in July 2015 I've not had any pain or cramping of the right foot. My wife and I have gone on long and hard hikes with no discomfort to me. I still have the nodules, but they are softer and smaller. I'm very happy that I took this path for treatment. I knew from the outset that Dr. Bocian could not promise the fibroma would go away but the pain and discomfort did. Thank you Dr. Bocian and Natasha."

EXAMPLE 6

This Example 6 comprises an unsolicited testimonial from a patient of Applicant.

"I told Dr. Bocian I was experiencing pain on the arch of my left foot. He sent me for a diagnostic ultrasound and explained I had Plantar Fibromatosis. He suggested I try a fairly new laser treatment. I elected to follow his advice and get the laser treatment rather than having surgery to remove the fibromas.

My foot was so sensitive Dr. Bocian could barely touch it without me jumping out of my chair. Honestly, I was a little skeptical. The first treatment was awful and left me in tears. I was not looking forward to the remaining treatments but knew I had to go through with them due to the pain I was experiencing and the affect it was having on my quality of life.

With each treatment, my foot was getting better and there was less and less pain. By the ninth treatment I was 100% better, the laser worked wonderfully and I couldn't be happier. I'm so glad I continued the treatment each week. Jam back to dancing and getting my quality of life back.

When I went back to get my follow-up diagnostic ultrasound at University of Arizona Medical Center, the tech remembered me and told me she couldn't believe the difference. She said when she did my first ultrasound, I would pull my foot away and now she was able to press on my foot and there was no pain.

I want to thank Dr. Bocian and Natasha for being so patient with me. My treatments took longer than normal due to the sensitivity of my foot and they had to keep stopping. I would recommend this treatment to anyone experiencing Plantar Fibromatosis and to not get discouraged after the first treatment! It gets better! Thank you again!"

EXAMPLE 7

This Example 7 comprises an unsolicited testimonial from a patient of Applicant.

"I'm a nurse who works long 12 hour shifts. I began having pain in the arch and heel of my right foot a year and a half ago. As time went on, the pain got increasingly worse. The pain began affecting my daily life. I had spent hundreds of dollars on shoes, pain creams, and over the counter orthotics with no help. I finally went to see Dr. Bocian and was given all options from orthotics, laser, and surgery. Surgery was not an option for me due to cost and down time. I opted for the custom orthotics and laser. The price was much more affordable and no down time!I will admit that I was a little skeptical about the laser at first, but I trusted in Dr. Bocian that this will work. By the time my treatment coarse came to an end, I was amazed how well the laser worked! I am now back to doing the things in life that I had stopped doing because of the foot pain. I owe Dr. Bocian and his laser technician Natasha a huge thank you!"

EXAMPLE 8

This Example 8 comprises an unsolicited testimonial from a patient of Applicant.

"I am extremely happy with my laser treatment given by Dr. Bocian and Natasha, his assistant, for my painful plantar fibroma. They are both very skilled in using the laser and it is a very good option for this painful condition.

It took away the discomfort and caused it to shrink away to almost nothing. I am back to walking and jogging and was able to do 6.6 miles with no problem. Thanks again! I highly recommend Dr. Bocian's laser treatment for Plantar Fibroma."

EXAMPLE 9

This Example 9 comprises an unsolicited testimonial from a patient of Applicant.

"Last July I limped into your office with a lump on the sole of my foot and in severe pain. You diagnosed the lump as plantar fibroma. I had a trip to Yellowstone planned in 4 weeks, so you immediately started me on a series of laser treatments. The fibroma improved sufficiently in 4 weeks, so that I was able to enjoy my trip.

Today, after 13 laser treatments, I am back to all my normal activities which includes walking for exercise. I would definitely recommend laser treatment for anyone suffering from plantar fibroma."

Additional Implementations, Including Other Lasing Devices:

Various different lasing devices and treatment processes may also be utilized to provide improved treatment of a subject fibrous mass, such as treatment regimens that involve even fewer treatments sessions for any given patient. For example, the following treatment processes have been found to treat a patient and achieve a cured state in as few as 6-7 treatments, such as for situations where the fibrous mass does not involve factors that complicate achieving a relieved/cured state, to approximately 9-11 treatments for situations where several complicating factors are present, to even more treatments needed in situations where severe complication exist such that each laser treatment session provides substantially less efficacy due to factors that prevent the laser application from softening and/or reducing the size of the fibrous mass.

In general, according to these further embodiments, parameters of the laser treatment methods for treating a fibrous mass of plantar fascia can be varied for different types of conditions. For example, various parameters may be varied within defined ranges to treat: (A) Plantar Fibromatosis, which is a thickening or nodule typically within the central portion of the medial limb of the plantar fascia composed mostly of Type III collagen (etiology unknown); (B) chronic plantar fasciopathy, which is a thickening of the proximal portion of the plantar fascia just distal to its insertion into the os calcis (here, for example, thickening results from repetitive micro-trauma or tearing of the fascia at its weak point leading to scarring or fibrosis composed mainly of Type III collagen). Etiology unknown refers to the cause of plantar fibromatosis. There is no known cause for plantar fibromatosis. Although, it has been associated with trauma, liver disease, diabetes mellitus, epilepsy and alcoholism, there is no direct relationship with these disorders; (C) Morton's neuroma or stump neuroma; and (D) Achilles tendinopathy, among others.

Clinical and pathologic studies have classified plantar fibromatosis into three stages: proliferative, involutional, and residual. The first stage is described by cellular proliferation, the second stage by nodule formation, and the third stage by tissue contraction. Histologic findings associated with fibromatosis include myofibroblastic proliferation with elongated oval-shaped nuclei and a preponderance of type III collagen.

In certain embodiments, both below and above (i.e., any/all implementations of the disclosed technology including a topical medication, including the embodiments/figures, above), a topical medication that may have various formulations can be applied directly on the skin, e.g., at the location of the fibrous mass/treatment. In some aspects, the topical medication may be selected from a group consisting of cream, gel, ointment, and lotion. According to certain embodiments, the applying the topical medication step further comprises using a combination of topical medications comprising verapamil, pentoxifylline, and/or tranilast. In one specific embodiment, the applying the topical medication step further comprises using about 15% verapamil by weight, about 3% pentoxifylline by weight, and about 1% tranilast by weight. In other specific embodiments, the applying the topical medication step further comprises using about 15% verapamil by volume, about 3% pentoxifylline by volume, and about 1% tranilast by volume. Further, in some implementations, the topical medication may comprise variations such as: about 15% verapamil (by weight or volume), about 3% pentoxifylline (by weight or volume), and tranilast; or about 15% verapamil (by weight or volume), about 1% tranilast (by weight or volume), and pentoxifylline; or about 3% pentoxifylline (by weight or volume), about 1% tranilast (by weight or volume), and verapamil; or 10-20% verapamil (by weight or volume), 1-5% pentoxifylline (by weight or volume), and 0.25-2% tranilast (by weight or volume); or 12-18% verapamil (by weight or volume), 2-4% pentoxifylline (by weight or volume), and 0.5-1.5% tranilast (by weight or volume); or 10-20% verapamil (by weight or volume), 1-5% pentoxifylline (by weight or volume), and tranilast or a chemical equivalent thereof; or 10-20% verapamil (by weight or volume), 0.25-2% tranilast (by weight or volume), and pentoxifylline or a chemical equivalent thereof; or 1-5% pentoxifylline (by weight or volume), 0.25-2% tranilast (by weight or volume), and verapamil or a chemical equivalent thereof; or 10-20% verapamil (by weight or volume) and 1-5% pentoxifylline (by weight or volume); or 10-20% verapamil (by weight or volume) and 0.25-2% tranilast (by weight or volume); or 1-5% pentoxifylline (by weight or volume) and 0.25-2% tranilast (by weight or volume); or a formulation with "about" the noted numerical quantities of all the above-listed permutations and their subcomponents.

Similarly, while certain illustrative numerical values and/or numerical ranges are frequently used for certain parameters, such depth of treatment and frequency, it should be understood that variations of such numbers are still within the ambit of the innovations herein, especially when all or most of the other parameters fall within the noted/specified ranges. As far as depth of penetration to reach the Fibrous Mass, for example, this depth is typically in the range of 6-8 mm, though obviously can vary based on the patient and the condition of the foot. Some patients have a very thick heel pad or fat pad and thus, the depth may need to be adjusted, even beyond 8 mm in some instances. Similarly, while a frequency of 7 Hz is often utilized, it is to be understood that some variation or change in such numerical value is certainly possible in some implementations of the present innovations. No such single numerical figure is necessarily present in all embodiments, particularly when not delineated in a recited invention.

The following parameters may be varied based on the medical condition of the fibrous mass, including: (A) spot size: Modifying the spot size will change the depth of penetration of the laser. Increase spot size will allow deeper tissue penetration and use least amount of energy at the surface thus limiting side effects to surface tissue. Larger spot size reduces scatter resulting in more photons delivered to target tissue; (B) pulse width: A smaller fibrous mass will require less pulse width time, 0.3 msec. A larger fibrous mass will require more pulse width time, 0.5 msec; (C) power density: Power and spot size when combined create power density. Power density is the equivalent to the amount of energy and heat delivered to the target tissue. The power density can be adjusted depending upon the size of the fibrous mass and the location of the fibrous mass in respect to the distance from the skin surface; and/or (D) optionally, cooling: Cooling of tissue protects the superficial layers of skin allowing the laser to penetrate deeper into target tissue with less adverse sensation, effect, or perceived effect/sensation, especially in the dermis or outer layer of the foot. If the fibrous mass is small, additional cooling is utilized to protect adverse effects to superficial tissue. The greater degree of cooling, the more profound effect of skin protection is achieved. Advantageously, implementations herein are selected with fluence/power density and/or other parameter settings such that the energy/heat being delivered does not raise to the level of requiring cooling, such as (esp.) prior to a first treatment. In many instances, the high intensity laser penetrates to the treatment area well below the dermis and no amount of cooling can help the discomfort felt by the high intensity laser. However, some patients do like the effect of such cooling/cooling tip, thus some of the implementations herein may include such features.

Further, factors that can determine which parameter settings are utilized may include size of the lesion, chronicity of the condition, and thickness of plantar fat pad, among others. With regard to the size of the lesion, a larger lesion will be treated more efficiently/effectively using a larger spot size. The size of the lesion may be determined by imaging techniques, such as diagnostic ultrasound imaging. With regard to chronicity of the condition, typically the longer the symptoms of the fibrous mass condition, such as plantar fasciitis/plantar fasciopathy, Morton's neuroma, etc., have been present, the larger the area of fibrosis will need to be treated. The thickness of the plantar fascia and size of the Morton's neuroma will typically increase in size the longer symptoms have been present. These findings are visualized on diagnostic ultrasound imaging. Adjustments are made in fluence or power density (e.g., J/cm2, etc.) and other laser parameters set forth herein such as spot size to accommodate/adjust for the various findings, here. With regard to the thickness of plantar fat pad, the thickness of the plantar fad pad can be determined via manual techniques as well as medical diagnostics such as imaging, e.g., diagnostic ultrasound. According to some implementations, suitable/proper adjustments may be made in the spot size to accommodate for any significant variances in the fat pad thickness. In many instances, the plantar fat pad thickness is an important factor when treating both Morton's neuroma, stump neuroma and chronic plantar fasciitis/plantar fasciopathy.

Innovations herein may also include or involve Shear Wave Elastography Imaging (SWEI), which can be used to evaluate soft tissue elasticity, especially in that SWEI may be utilized to expressly and tacitly measure beneficial results of the treatment methods herein. SWEI is an objective and quantitative tool which can be used for measuring tissue's elastic properties. Comparison SWEI of fibrous masses associated with plantar fibromatosis and chronic plantar fasciitis (plantar fasciopathy) before and after the innovative laser treatment processes herein have demonstrated a slowing of the velocity of the shear waves post treatment consistent with a softening and increase in elasticity of the tissue.

Figure 6:
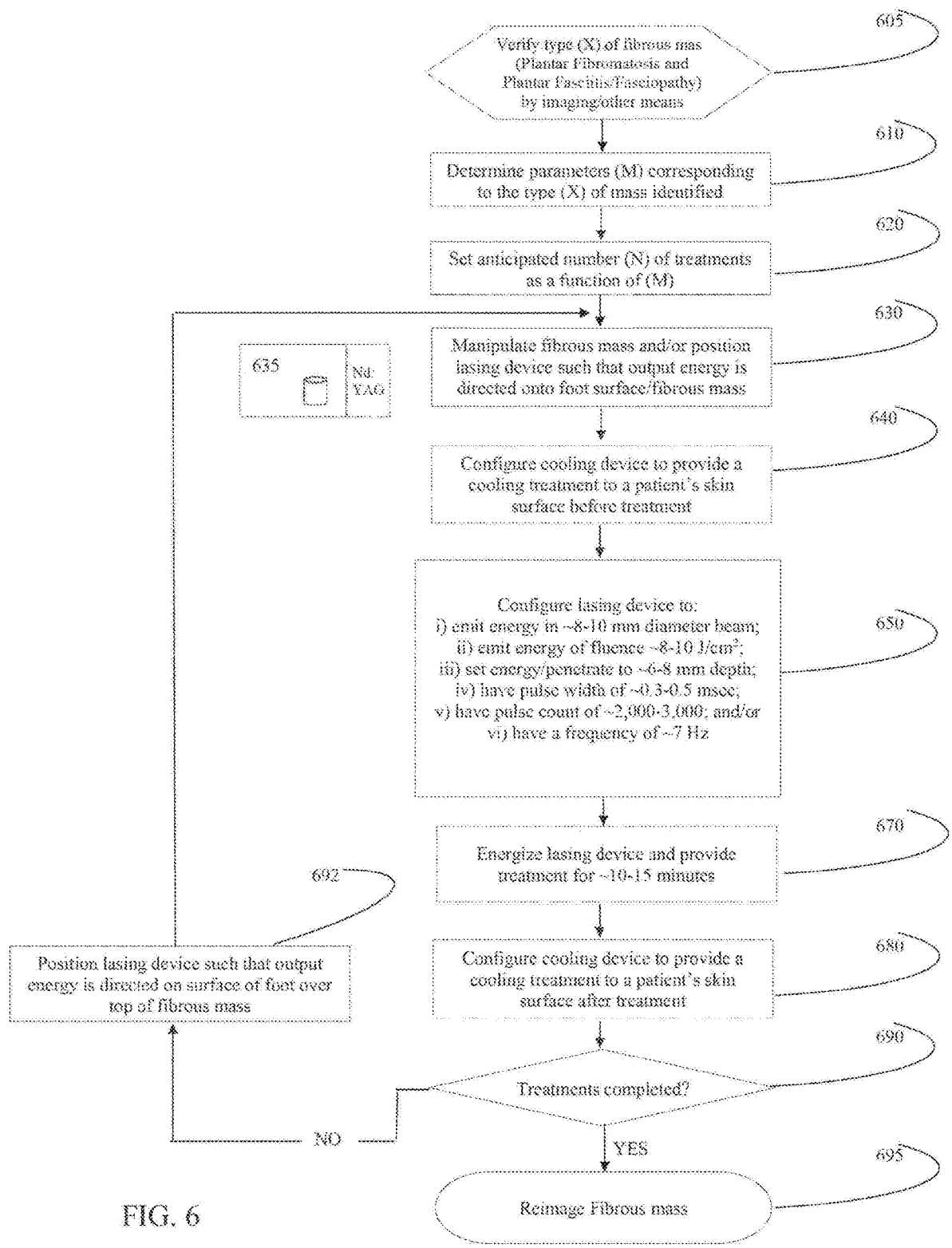
FIG. 6 is a diagram of other embodiments for treating Plantar Fibromatosis and Plantar Fasciitis/Fasciopathy, according to aspects of the innovations herein.
Figure 7:
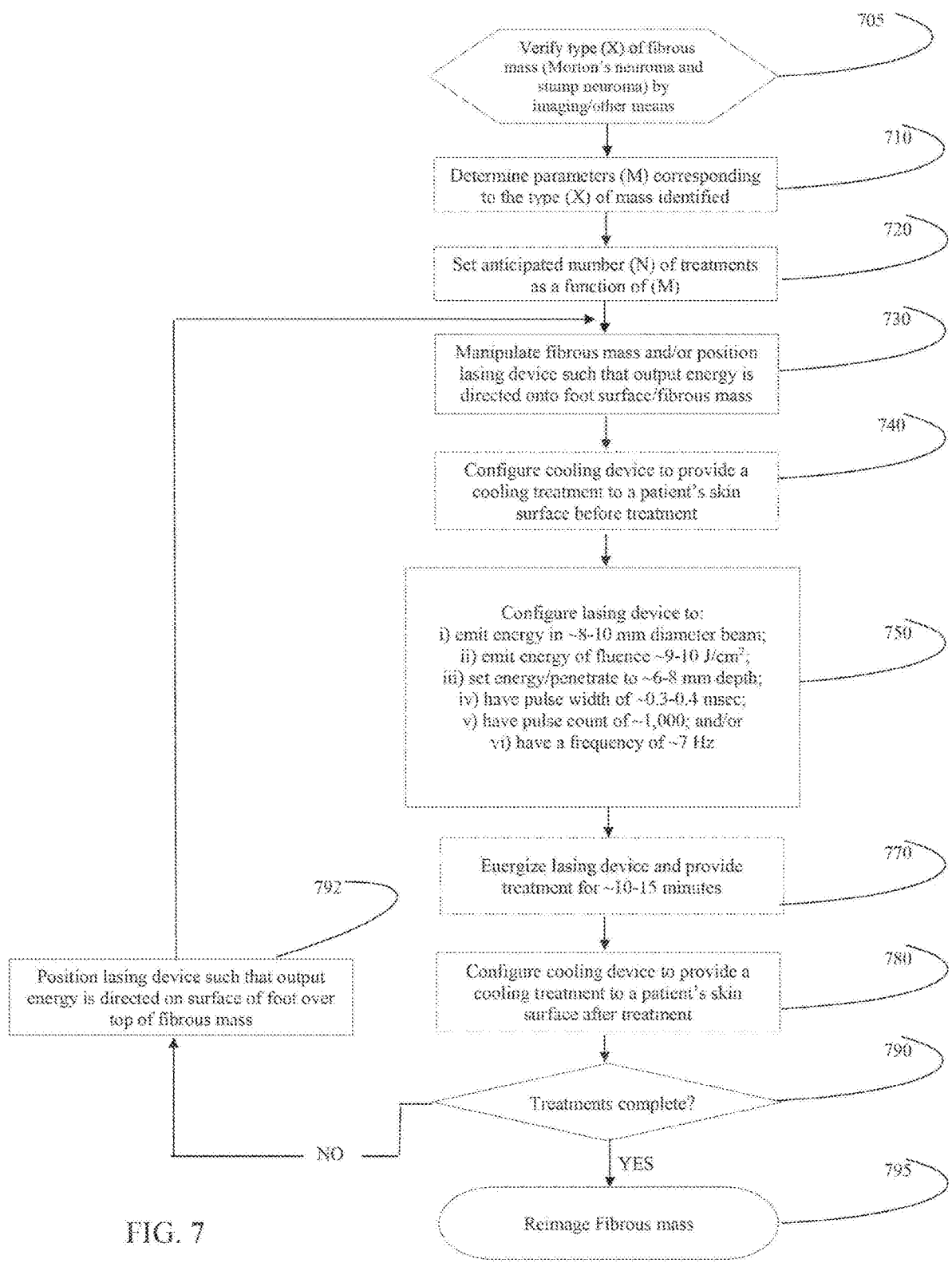
FIG. 7 is a diagram of other embodiments for treating Morton's neuroma including stump neuroma, according to aspects of the innovations herein.
Figure 8:
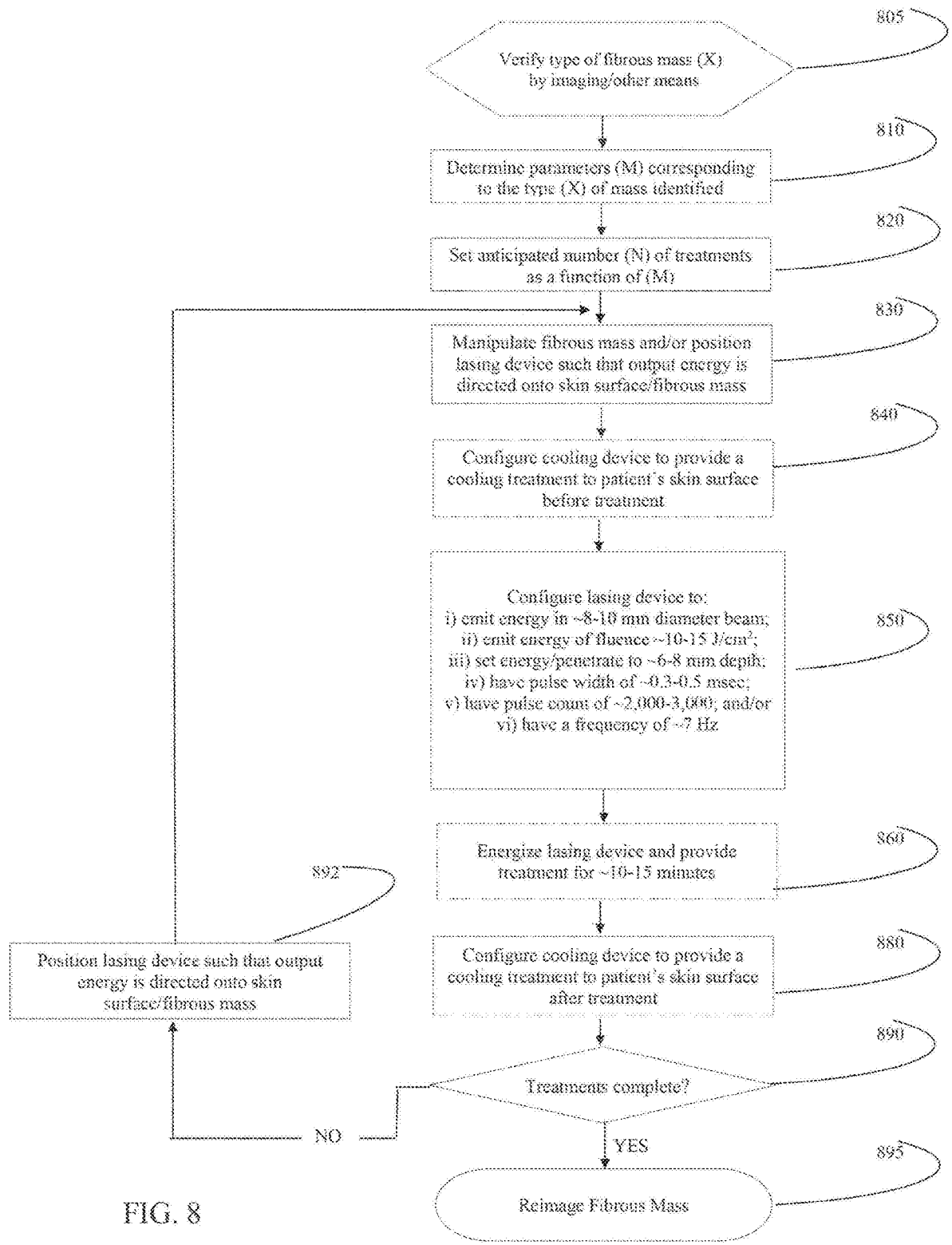
FIG. 8 is a diagram of other embodiments for treating injury associated with Achilles tendinopathy, according to aspects of the innovations herein.

In the embodiments of FIGS. 6-8, below, the overall parameters/parameter ranges may be initially specified based on the type of mass (ailment) identified. Further, for the parameters that should be set within a specified range, various factors of the mass, ailment/injury, and patient (both the physical body and sometimes otherwise) need to be taken into account to select a best numerical/specific parameter from within the parameter range. For example, with regard to beam diameter, the spot size from among the 8-10 mm range is varied and set based on one or both of depth of penetration needed (a higher spot size yields deeper penetration), and/or the laser's effects on the patient's surface tissue (increased spot size equates to less surface damage), the latter of which often also involves an assessment of the particular patient's discomfort and/or pain thresholds, both actual and also sometimes perceived or subjective. The depth of treatment, typically 6-8 mm, is varied based on the location (generally depth) of the mass. The energy (fluence or power density) is varied based on one or both of the size of the mass and/or the location or depth of the mass, with this location/depth typically being distance from skin surface though factors such as thickness of heel pad(s) or fat pad(s) must be factored-in when applicable. Further, the pulse width selected from within the relevant range may be determined based on the size of the mass.

Treatment of Plantar Fibromatosis and Plantar Fasciitis/Fasciopathy:

In certain embodiments, the delivering electromagnetic energy to the fibrous mass step may comprise emitting electromagnetic energy from a lasing device in a beam diameter of spot size of a selected size. Namely, here, for treatment of Plantar Fibromatosis and Plantar Fasciitis/Fasciopathy, the spot size is typically selected in a range of 8-10 mm. Power and/or other parameters of the lasing device may be adjusted such that the electromagnetic energy penetrates tissues to a depth of about 6 mm to about 8 mm. Further, the beam may be directed onto the treatment location for a length of time of about 10 minutes to about 15 minutes, and about 2,000-3,000 pulses of the beam may be delivered to the location. In some embodiments, a Nd:YAG lasing device can be utilized.

FIG. 6 refers to embodiments of the present innovations. FIG. 6 illustrates a treatment device or laser device 635 according to the disclosed inventions and a method of treating a fibrous mass 605-695 according to aspects of the innovations herein. In certain embodiments, the treatment device 635 of all embodiments of the disclosed technology may include a Nd:YAG laser. The method may comprise verifying a type (X) of fibrous mass 605 (i.e., here, Plantar Fibromatosis and Plantar Fasciitis/Fasciopathy) by imaging and/or other means known in the art, determining parameters (M) corresponding to the type (X) of mass identified 610, and setting anticipated number (N) of treatments as a function of (M) 620. In step 630, the method may include manipulating the fibrous mass and/or positioning the lasing device such that output energy is directed onto foot surface/fibrous mass. In step 640, the method may optionally include a step of providing a cooling treatment to the patient's skin before a laser treatment.

In step 650, the method configures the lasing device to emit electromagnetic energy onto the fibrous mass/patient's foot surface at specified parameters. For example, to treat such plantar fibromatosis and plantar fasciitis/plantar fasciopathy, the treatment/laser device may be configured such that: the energy is emitting in about a 8-10 mm diameter beam/spot size; the energy output (e.g., fluence, power density) is about 8-10 J/cm$^2$; the energy penetrates the patient's tissue to about a 6-8 mm depth; the energy has a pulse width of about 0.3-0.5 msec; the laser output has a pulse count of about 2,000-3,000; and/or the output laser energy has a frequency of about 7 Hz. In the embodiment of FIG. 6 (plantar fibromatosis and plantar fasciitis/plantar fasciopathy treatment), the pulse count, e/g/from among the specified range, is advantageously set/varied as a function of one or both of the size of the fibrous mass and/or the quantity of lesions. Further, the duration of treatment is advantageously set/varied as a function of one or both of the size of the fibrous mass and/or the patient's discomfort/pain tolerance level(s).

In step 670, the method energizes the lasing device for about 10 to about 15 minutes.

In step 680 in certain embodiments, the method may, optionally, include providing a cooling treatment to the patient's skin after a laser treatment.

In step 690, the method determines if (i) equals (N). If the method determines in step 690, that (i) does not equal (N), then the method transitions from step 690 to step 692 wherein the method increments (i) by 1, i.e. sets (i) equal to (i+1), The method then transitions from step 692 to step 630 and continues as described herein.

If the method determines in step 690, that (i) does equal (N), then the method transitions from step 690 to step 695 wherein the process may include a step of reimaging the Plantar Fibromatosis or Plantar Fasciitis/Fasciopathy, which may comprise use of SWEI imaging.

Treatment of Morton's Neuroma and Stump Neuroma:

In certain embodiments, the delivering electromagnetic energy to the fibrous mass step further comprises emitting electromagnetic energy from a lasing device in a beam diameter of spot size of a selected size. Namely, here, for treatment of Morton's neuroma including stump neuroma, a spot size of ~8-10 mm may be utilized. Further, the power and/or other parameters of the lasing device may be adjusted such that electromagnetic energy is delivered as described further below, such as to penetrate tissues to a depth of about 6 mm to about 8 mm, direct the beam onto the location for a length of time of about 10 minutes to about 15 minutes, and/or deliver about 1,000 pulses of the beam to the location, inter alia. In some embodiments, a Nd:YAG lasing device can be utilized.

In certain embodiments, the lasing device 635 used in the embodiment of FIG. 7 may comprises a Nd:YAG laser.

FIG. 7 refers to an embodiment of the present innovations. FIG. 7 illustrates a method of treating a fibrous mass 705-795 using a treatment device 635 according to aspects of the innovations herein. The method may comprise verifying a type (X) of fibrous mass 705 (i.e., here, Morton's neuroma and stump neuroma) by imaging and/or other means known in the art, determining parameters (M) corresponding to the type (X) of mass identified 710, and setting anticipated number (N) of treatments as a function of (M) 720. In step 730, the method may include manipulating the fibrous mass and/or positioning the lasing device such that output energy is directed onto foot surface/fibrous mass. In step 740, the method may optionally include a step of providing a cooling treatment to the patient's skin before a laser treatment.

In step 750, the method configures the lasing device to emit electromagnetic energy onto the fibrous mass/patient's foot surface at specified parameters. For example, to treat such Morton's neuroma and stump neuroma, the treatment/laser device may be configured such that: the energy is emitting in about a 8-10 mm diameter beam/spot size; the energy output (e.g., fluence, power density) is about 9-10 J/cm$^2$; the energy penetrates the patient's tissue to about a 6-8 mm depth; the energy has a pulse width of about 0.3-0.4 msec; the laser output has a pulse count of about 1,000; and/or the output laser energy has a frequency of about 7 Hz. In the embodiment of FIG. 7 (Morton's neuroma and stump neuroma treatment), the duration of treatment is advantageously set/varied as a function of one or both of the size of the fibrous mass and/or the patient's discomfort/pain tolerance level(s).

In step 770, the method energizes the lasing device for about 10 to about 15 minutes.

In step 780 in certain embodiments, the method may, optionally, include providing a cooling treatment to the patient's skin after a laser treatment.

In step 790, the method determines if (i) equals (N). If the method determines in step 790, that (i) does not equal (N), then the method transitions from step 790 to step 792 wherein the method increments (i) by 1, i.e. sets (i) equal to (i+1), The method then transitions from step 792 to step 730 and continues as described herein.

If the method determines in step 790, that (i) does equal (N), then the method transitions from step 790 to step 795 wherein the method reimages the Morton's neuroma including stump neuroma.

Treatment of Achilles Tendinopathy:

As set forth in more detail, below, the disclosed technology also includes treatment methods for curing/relieving Achilles tendinopathy. This foot ailment is related to a similar type of underlying issue/growth, i.e. a fibrous mass (although located in the Achilles tendon), which can be treated by the presently-disclosed Bocian Achilles technique, similar to the present treatments of Morton's Neuroma, Stump Neuroma, Plantar Fasciitis, Plantar Fibromatosis, etc. Further, evidence and proof based on testing done using Shear Wave Elastography (SWEI), further demonstrates that the treatment processes herein can cure/relieve Achilles tendinopathy. Moreover, it is noted that this present treatment for Achilles tendinopathy is not only very effective, but is also the only non-invasive treatment available for patients having Achilles Tendinopathy.

With regard to Achilles tendinopathy, according to certain embodiments, the delivering electromagnetic energy to the fibrous mass step may comprise emitting electromagnetic energy from a lasing device in a beam diameter of spot size of a selected size. Namely, here, for treatment Achilles tendinopathy, a size of about 8-10 mm may be utilized. Further, various parameters may be adjusted as set forth in full detail, below. For example, the power of the lasing device may be adjusted such that the electromagnetic energy penetrates tissues to a depth of about 6 mm to about 8 mm, the beam may be directed onto the location/mass for a length of time of about 10 minutes to about 15 minutes, and about 2,000-3,000 pulses of the beam may be delivered to the location/mass, inter alia. In some embodiments, the lasing device 635 utilized in the embodiment of FIG. 8 may include a Nd:YAG laser.

FIG. 8 refers to another embodiment of the present innovations. FIG. 8 illustrates a method of treating a fibrous mass 805-895 using a treatment device 635 according to aspects of the innovations herein. The method may comprise verifying a type (X) of fibrous mass 805 (i.e., here, Achilles tendinopathy) by imaging and/or other means known in the art, determining parameters (M) corresponding to the type (X) of mass identified 810, and setting anticipated number (N) of treatments as a function of (M) 820. In step 830, the method may include manipulating the fibrous mass and/or positioning the lasing device such that output energy is directed onto foot surface/fibrous mass. In step 840, the method may optionally include a step of providing a cooling treatment to the patient's skin before a laser treatment.

In step 850, the method configures the lasing device to emit electromagnetic energy onto the fibrous mass/patient's foot surface at specified parameters. For example, to treat such Achilles tendinopathy, the treatment/laser device may be configured such that: the energy is emitting in about a 8-10 mm diameter beam/spot size; the energy output (e.g., fluence, power density) is about 10-15 J/cm²; the energy penetrates the patient's tissue to about a 6-8 mm depth; the energy has a pulse width of about 0.3-0.5 msec; the laser output has a pulse count of about 2,000-3,000; and/or the output laser energy has a frequency of about 7 Hz. In the embodiment of FIG. 8 (Achilles tendinopathy), the duration of treatment is advantageously varied/set as a function of one or both of the size of the fibrous mass and/or the patient's discomfort/pain tolerance level(s).

In step 870, the method energizes the lasing device for about 10 to about 15 minutes.

In step 880 in certain embodiments, the method may, optionally, include providing a cooling treatment to the patient's skin after a laser treatment.

In step 890, the method determines if (i) equals (N). If the method determines in step 890, that (i) does not equal (N), then the method transitions from step 890 to step 892 wherein the method increments (i) by 1, i.e. sets (i) equal to (i+1), The method then transitions from step 892 to step 830 and continues as described herein.

If the method determines in step 890, that (i) does equal (N), then the method transitions from step 890 to step 895 wherein the method reimages the Achilles tendinopathy.

Figure 9:
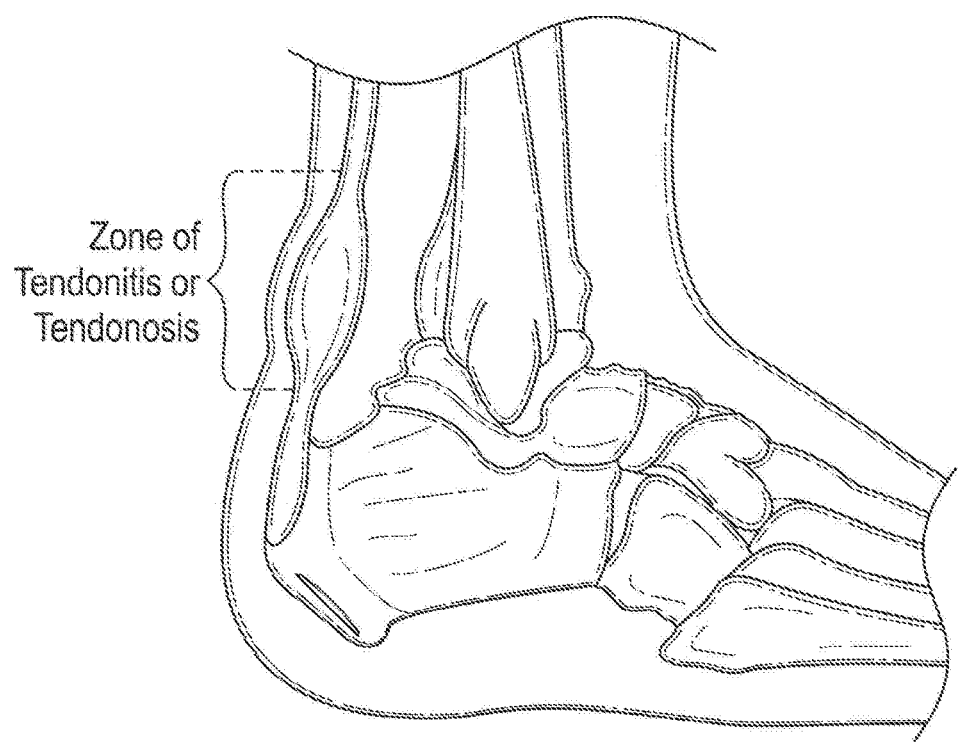
FIG. 9 illustrates the anatomy of the Achilles tendonitis or tendonosis.

FIG. 9 illustrates the anatomy of the Achilles tendonitis or tendonosis.

As used herein, the term "about" when used in connection with numerical parameters in the claims carries its accepted meaning as established by well-known construction of such expression by courts including the CAFC, e.g., a 10% variance of the stated upper/lower bounds, again, as known in established claim construction tenets.

While various illustrative implementations of the present innovations have been illustrated in detail, it should be apparent that modifications and adaptations to those embodiments may occur to one skilled in the art without departing from the scope of the present inventions.

The invention claimed is:

1. A method for treating a fibrous mass comprised of Achilles tendinopathy in a human foot, the method comprising:
   identifying a location of the fibrous mass in the foot using a medical imaging technique;
   non-surgically delivering electromagnetic energy to the located fibrous mass during a treatment of a plurality of treatments of the foot, each treatment including:
   emitting electromagnetic energy from a laser in a beam having a frequency of 7 Hz;
   adjusting a power (fluence) of the laser in a range of 10 J/cm² to 15 J/cm²;
   directing the beam of the laser over an 8 mm to 10 mm diameter spot on a skin surface of the foot such that the beam irradiates the location of the fibrous mass;
   delivering at least 2,000 pulses of the laser to the location, per treatment;
   applying the pulses of a pulse width of 0.3 msec to 0.5 msec; and
   directing the beam onto the location to irradiate the fibrous mass for 10 minutes; and
   performing 6 of the treatments, and thereby reducing a size of the fibrous mass and softening the fibrous mass to an extent such that a recipient is relieved of disability resulting from the fibrous mass beyond mere reduction in a pain level associated with the fibrous mass.

2. The method of claim 1 wherein each treatment further includes:
   applying a topical medication directly on a skin surface at a location where each treatment of the located fibrous mass is being administered, wherein the topical medication comprises two or more of verapamil, pentoxifylline, and/or tranilast.

3. The method of claim 1 wherein each treatment further includes:
   delivering between 2,000 and 3,000 pulses of the laser to the location, per treatment.

4. The method of claim 1, wherein each treatment of the plurality of treatments further comprises:
   delivering at least 3,000 pulses of the laser to the location, per treatment.

5. The method of claim 1, wherein each treatment of the plurality of treatments further comprises directing the beam of an 8 mm diameter spot size onto the skin surface of the foot.

6. The method of claim 1, wherein using medical imaging techniques further comprises using magnetic resonance imaging.

7. The method of claim 1, further comprises using a Nd:YAG lasing device.

8. The method of claim 1, wherein, as a result of administering the plurality of the treatments, size of the fibrous mass is reduced at least 33% in measure in at least one dimension, as determined via comparison of a first image taken via the medical imaging technique before the plurality of treatments are administered and a second image taken via the medical imaging technique after the plurality of treatments are administered.

9. The method of claim 1, wherein, as result of the plurality of treatments, the fibrous mass is diffused in density or shape, as determined via comparison of a first image taken via the medical imaging technique before the plurality of treatments are administered and a second image taken via the medical imaging technique after the plurality of treatments are administered.

10. The method of claim 1, wherein the power of the laser is adjusted between 10 J/cm² and about 12 J/cm² for each treatment of the plurality of treatments.

11. The method of claim 1, wherein the laser delivers laser energy having a power density less than or equal to 15 J/cm² that is characterized as being less than a fluence at which pre-cooling of a treatment area prior to each treatment of the plurality of treatments is performed in order to avoid overheating the recipient's flesh and to thereby maintain recipient comfort.

12. The method of claim 1 wherein, as a result of administering the plurality of the treatments, a size of the fibrous mass is reduced by at least 0.1 cm in at least one dimension, as determined via comparison of a first image taken via the medical imaging technique before the plurality of treatments are administered and a second image taken via the medical imaging technique after the plurality of treatments are administered.

13. The method of claim 1, wherein each treatment further includes:
   directing the beam onto the location to irradiate the fibrous mass for 15 minutes.

14. The method of claim 1, further comprising:
   performing 7 of the treatments, and thereby reducing a size of the fibrous mass and softening the fibrous mass to an extent such that the recipient is relieved of disability resulting from the fibrous mass beyond mere reduction in a pain level associated with the fibrous mass.

15. The method of claim 14, wherein each treatment further includes:

delivering between 2,000 and 3,000 pulses of the laser to the location, per treatment.

16. The method of claim 14, wherein each treatment further includes:
delivering at least 3,000 pulses of the laser to the location, per treatment.

17. The method of claim 14, wherein each treatment further includes:
directing the beam of an 8 mm diameter spot size onto the skin surface of the foot.

18. The method of claim 14, wherein using medical imaging techniques further comprises using magnetic resonance imaging.

19. The method of claim 14, wherein the laser includes a Nd:YAG lasing device.

20. The method of claim 14, wherein, as a result of administering the plurality of the treatments, size of the fibrous mass is reduced at least 33% in measure in at least one dimension, as determined via comparison of a first image taken via the medical imaging technique before the plurality of treatments are administered and a second image taken via the medical imaging technique after the plurality of treatments are administered.

21. The method of claim 14, wherein, as result of the plurality of treatments, the fibrous mass is diffused in density or shape, as determined via comparison of a first image taken via the medical imaging technique before the plurality of treatments are administered and a second image taken via the medical imaging technique after the plurality of treatments are administered.

22. The method of claim 14, wherein the power of the laser is adjusted between 10 J/cm$^2$ and about 12 J/cm$^2$ for each treatment of the plurality of treatments.

23. The method of claim 14, wherein the laser delivers laser energy having a power density (fluence) that is characterized as being less than a fluence at which pre-cooling of a treatment area prior to each treatment of the plurality of treatments is performed in order to avoid overheating the recipient's flesh and to thereby maintain patient comfort.

24. The method of claim 14, wherein each treatment further includes:
directing the beam onto the location to irradiate the fibrous mass for 15 minutes.

25. The method of claim 14, wherein, as a result of administering the plurality of the treatments, a size of the fibrous mass is reduced by at least 0.1 cm in at least one dimension, as determined via comparison of a first image taken via the medical imaging technique before the plurality of treatments are administered and a second image taken via the medical imaging technique after the plurality of treatments are administered.

26. A method for treating a fibrous mass comprised of Achilles tendinopathy in a human foot, the method comprising:
identifying a location of the fibrous mass in the foot;
non-surgically delivering electromagnetic energy from a laser to the located fibrous mass during a treatment of a plurality of treatments of the foot, each treatment including:
adjusting a power (fluence) of the laser in a range of 10 J/cm$^2$ to 15 J/cm$^2$;
directing a beam of the laser over an 8 mm to 10 mm diameter spot on a skin surface of the foot such that the beam irradiates the location of the fibrous mass;
delivering at least 2,000 pulses of the laser to the location, per treatment;
applying the pulses of a pulse width of 0.3 msec to 0.5 msec; and
directing the beam onto the location to irradiate the fibrous mass for 10 minutes; and
performing 6 of the treatments, and thereby reducing a size of the fibrous mass and softening the fibrous mass to an extent such that a recipient is relieved of disability resulting from the fibrous mass beyond mere reduction in a pain level associated with the fibrous mass.

27. The method of claim 26 wherein each treatment further includes:
emitting electromagnetic energy from a lasing device in a beam having a frequency of 7 Hz.

28. The method of claim 26 wherein each treatment further includes:
directing the beam onto the location to irradiate the fibrous mass for 15 minutes.

29. The method of claim 26, further comprising:
performing 8 of the treatments, and thereby reducing a size of the fibrous mass and softening the fibrous mass to an extent such that the recipient is relieved of disability resulting from the fibrous mass beyond mere reduction in a pain level-associated with the fibrous mass.

30. The method of claim 26, further comprising:
performing 7 of the treatments, and thereby reducing a size of the fibrous mass and softening the fibrous mass to an extent such that the recipient is relieved of disability resulting from the fibrous mass beyond mere reduction in a pain level-associated with the fibrous mass.

31. The method of claim 26, wherein the electromagnetic energy is adjusted between 10 J/cm$^2$ and 12 J/cm$^2$ for each treatment of the plurality of treatments.

32. The method of claim 26, wherein, as result of administering the plurality of treatments, the fibrous mass is diffused or reduced in size and/or shape, by at least 0.1 cm in at least one dimension, as determined via comparison of a first image taken via a medical imaging technique before the plurality of treatments are administered and a second image taken via the medical imaging technique after the plurality of treatments are administered.

33. The method of claim 26, wherein the laser includes a Nd:YAG lasing device.

34. The method of claim 26 wherein each treatment further includes:
delivering between 2,000 and 3,000 pulses of the laser to the location, per treatment.

35. The method of claim 26, wherein each treatment further includes:
delivering at least 3,000 pulses of the laser to the location, per treatment.

36. The method of claim 26, wherein, as a result of administering the plurality of the treatments, size of the fibrous mass is reduced at least 33% in measure in at least one dimension, as determined via comparison of a first image taken via a medical imaging technique before the plurality of treatments are administered and a second image taken via the medical imaging technique after the plurality of treatments are administered.

37. The method of claim 26, wherein, as result of the plurality of treatments, the fibrous mass is diffused in density or shape, as determined via comparison of a first image taken via a medical imaging technique before the plurality of treatments are administered and a second image taken via the medical imaging technique after the plurality of treatments are administered.

38. The method of claim 26, wherein the laser delivers laser energy having a power density (fluence) that is characterized as being less than a fluence at which pre-cooling of a treatment area prior to each treatment of the plurality of treatments is performed in order to avoid overheating the recipient's flesh and to thereby maintain patient comfort.

39. A method for treating a fibrous mass in a human foot, the method comprising:
 identifying a location of the fibrous mass in the foot;
 non-surgically delivering electromagnetic energy from a laser to the located fibrous mass during a treatment of a plurality of treatments of the foot, each treatment including:
  adjusting a power (fluence) of the laser in a range of 10 J/cm$^2$ to 15 J/cm$^2$;
  directing a beam of the laser over an 8 mm to 10 mm diameter spot on a skin surface of the foot such that the beam irradiates the location of the fibrous mass;
  delivering at least 2,000 pulses of the laser to the location, per treatment; and
  directing the beam onto the location to irradiate the fibrous mass for 10 minutes; and
 performing 6 of the treatments, and thereby reducing a size of the fibrous mass and softening the fibrous mass to an extent such that a recipient is relieved of disability resulting from the fibrous mass beyond mere reduction in a pain level associated with the fibrous mass.

40. The method of claim 39, wherein the laser includes a Nd:YAG laser.

41. The method of claim 40, wherein each treatment of the plurality of treatments further comprises directing the beam of an 8 mm diameter spot size onto the skin surface of the foot.

42. The method of claim 41, wherein each treatment further includes:
 emitting electromagnetic energy from a lasing device in a beam having a frequency of 7 Hz.

43. The method of claim 41, wherein each treatment further includes:
 emitting electromagnetic energy from a lasing device in a beam having a frequency of about 7 (6-8) Hz.

44. The method of claim 41, wherein the power of the laser is adjusted between 10 J/cm2 and about 12 J/cm2 for each treatment of the plurality of treatments.

45. The method of claim 41, wherein each treatment further includes:
 delivering between 2,000 and 3,000 pulses of the laser to the location, per treatment.

46. The method of claim 41, wherein each treatment further includes:
 delivering at least 3,000 pulses of the laser to the location, per treatment.

47. The method of claim 41, wherein each treatment further includes:
 directing the beam onto the location to irradiate the fibrous mass for 15 minutes.

48. The method of claim 40, wherein the power of the laser is adjusted between 10 J/cm2 and about 12 J/cm2 for each treatment of the plurality of treatments.

49. The method of claim 48, wherein each treatment further includes:
 delivering between 2,000 and 3,000 pulses of the laser to the location, per treatment.

50. The method of claim 48, wherein each treatment further includes:
 delivering at least 3,000 pulses of the laser to the location, per treatment.

51. The method of claim 48, wherein each treatment further includes:
 directing the beam onto the location to irradiate the fibrous mass for 15 minutes.

52. The method of claim 40, wherein each treatment further includes:
 delivering between 2,000 and 3,000 pulses of the laser to the location, per treatment.

53. The method of claim 40, wherein each treatment further includes:
 delivering at least 3,000 pulses of the laser to the location, per treatment.

54. The method of claim 40, wherein each treatment further includes:
 directing the beam onto the location to irradiate the fibrous mass for 15 minutes.

55. The method of claim 39, wherein each treatment of the plurality of treatments further comprises directing the beam of an 8 mm diameter spot size onto the skin surface of the foot.

56. The method of claim 39, wherein each treatment further includes:
 emitting electromagnetic energy from a lasing device in a beam having a frequency of 7 Hz.

57. The method of claim 39, wherein the power of the laser is adjusted between 10 J/cm2 and about 12 J/cm2 for each treatment of the plurality of treatments.

58. The method of claim 39, wherein each treatment further includes:
 delivering between 2,000 and 3,000 pulses of the laser to the location, per treatment.

59. The method of claim 39, wherein each treatment further includes:
 delivering at least 3,000 pulses of the laser to the location, per treatment.

60. The method of claim 39, wherein each treatment further includes:
 directing the beam onto the location to irradiate the fibrous mass for 15 minutes.

61. The method of claim 39, further comprising:
 performing 7 of the treatments, and thereby reducing a size of the fibrous mass and softening the fibrous mass to an extent such that the recipient is relieved of disability resulting from the fibrous mass beyond mere reduction in a pain level associated with the fibrous mass.

62. The method of claim 61, wherein the laser includes a Nd:YAG laser.

63. The method of claim 62, wherein each treatment of the plurality of treatments further comprises directing the beam of an 8 mm diameter spot size onto the skin surface of the foot.

64. The method of claim 63, wherein each treatment further includes:
 emitting electromagnetic energy from a lasing device in a beam having a frequency of 7 Hz.

65. The method of claim 63, wherein each treatment further includes:
 emitting electromagnetic energy from a lasing device in a beam having a frequency of 7 Hz.

66. The method of claim 63, wherein the power of the laser is adjusted between 10 J/cm2 and about 12 J/cm2 for each treatment of the plurality of treatments.

67. The method of claim 63, wherein each treatment further includes:
 delivering between 2,000 and 3,000 pulses of the laser to the location, per treatment.

68. The method of claim 63, wherein each treatment further includes:
delivering at least 3,000 pulses of the laser to the location, per treatment.

69. The method of claim 63, wherein each treatment further includes:
directing the beam onto the location to irradiate the fibrous mass for 15 minutes.

70. The method of claim 62, wherein the power of the laser is adjusted between 10 J/cm2 and about 12 J/cm2 for each treatment of the plurality of treatments.

71. The method of claim 70, wherein each treatment further includes:
delivering between 2,000 and 3,000 pulses of the laser to the location, per treatment.

72. The method of claim 70, wherein each treatment further includes:
delivering at least 3,000 pulses of the laser to the location, per treatment.

73. The method of claim 70, wherein each treatment further includes:
directing the beam onto the location to irradiate the fibrous mass for 15 minutes.

74. The method of claim 62, wherein each treatment further includes:
delivering between 2,000 and 3,000 pulses of the laser to the location, per treatment.

75. The method of claim 62, wherein each treatment further includes:
delivering at least 3,000 pulses of the laser to the location, per treatment.

76. The method of claim 62, wherein each treatment further includes:
directing the beam onto the location to irradiate the fibrous mass for 15 minutes.

77. The method of claim 61, wherein each treatment of the plurality of treatments further comprises directing the beam of an 8 mm diameter spot size onto the skin surface of the foot.

78. The method of claim 61, wherein each treatment further includes:
emitting electromagnetic energy from a lasing device in a beam having a frequency of 7 Hz.

79. The method of claim 61, wherein the power of the laser is adjusted between 10 J/cm2 and about 12 J/cm2 for each treatment of the plurality of treatments.

80. The method of claim 61, wherein each treatment further includes:
delivering between 2,000 and 3,000 pulses of the laser to the location, per treatment.

81. The method of claim 61, wherein each treatment further includes:
delivering at least 3,000 pulses of the laser to the location, per treatment.

82. The method of claim 61, wherein each treatment further includes:
directing the beam onto the location to irradiate the fibrous mass for 15 minutes.

83. The method of claim 39, further comprising:
performing 8 of the treatments, and thereby reducing a size of the fibrous mass and softening the fibrous mass to an extent such that the recipient is relieved of disability resulting from the fibrous mass beyond mere reduction in a pain level-associated with the fibrous mass.

84. The method of claim 83, wherein the laser includes a Nd:YAG laser.

85. The method of claim 84, wherein each treatment of the plurality of treatments further comprises directing the beam of an 8 mm diameter spot size onto the skin surface of the foot.

86. The method of claim 85, wherein each treatment further includes:
emitting electromagnetic energy from a lasing device in a beam having a frequency of 7 Hz.

87. The method of claim 83, wherein each treatment of the plurality of treatments further comprises directing the beam of an 8 mm diameter spot size onto the skin surface of the foot.

88. The method of claim 83, wherein each treatment further includes:
emitting electromagnetic energy from a lasing device in a beam having a frequency of 7 Hz.

89. The method of claim 83, wherein the power of the laser is adjusted between 10 J/cm2 and about 12 J/cm2 for each treatment of the plurality of treatments.

90. The method of claim 83, wherein each treatment further includes:
delivering between 2,000 and 3,000 pulses of the laser to the location, per treatment.

91. The method of claim 83, wherein each treatment further includes:
delivering at least 3,000 pulses of the laser to the location, per treatment.

92. The method of claim 83, wherein each treatment further includes:
directing the beam onto the location to irradiate the fibrous mass for 15 minutes.

93. The method of any one of claims 39-86, wherein the pulses delivered have a pulse width of 0.3 msec to 0.5 msec.

94. The method of any one of claims 39-86, wherein, as a result of administering the plurality of the treatments, size of the fibrous mass is reduced at least 33% in measure in at least one dimension, as determined via comparison of a first image taken via a medical imaging technique before the plurality of treatments are administered and a second image taken via the medical imaging technique after the plurality of treatments are administered.

95. The method of any one of claims 39-86, wherein, as result of the plurality of treatments, the fibrous mass is diffused in density or shape, as determined via comparison of a first image taken via a medical imaging technique before the plurality of treatments are administered and a second image taken via the medical imaging technique after the plurality of treatments are administered.

96. The method of any one of claims 39-86, wherein, wherein the laser delivers laser energy having a power density (fluence) that is characterized as being less than a fluence at which pre-cooling of a treatment area prior to each treatment of the plurality of treatments is performed in order to avoid overheating the recipient's flesh and to thereby maintain recipient comfort.

97. The method of any one of claims 39-86, wherein, as a result of administering the plurality of the treatments, a size of the fibrous mass is reduced by at least 0.1 cm in at least one dimension, as determined via comparison of a first image taken via a medical imaging technique before the plurality of treatments are administered and a second image taken via the medical imaging technique after the plurality of treatments are administered.

* * * * *